United States Patent
Tsai et al.

(10) Patent No.: US 7,381,374 B2
(45) Date of Patent: Jun. 3, 2008

(54) IMMUNOASSAY DEVICES AND METHODS OF USING SAME

(75) Inventors: Hsiao-Chung Tsai, No. 23, Alley 18, Lane 77, Chongcing St., Bade City, Taoyuan County, 334 (TW); Hsueh-Chin Lin, Taipei (TW); Jen-Chieh Lin, Hsinchu (TW)

(73) Assignee: Hsiao-Chung Tsai, Taoyuan County (TW)

( * ) Notice: Subject to any disclaimer, the term of this patent is extended or adjusted under 35 U.S.C. 154(b) by 408 days.

(21) Appl. No.: 10/945,960

(22) Filed: Sep. 22, 2004

(65) Prior Publication Data

US 2006/0063251 A1    Mar. 23, 2006

(51) Int. Cl.
*B01L 3/00* (2006.01)

(52) U.S. Cl. .................. 422/102; 422/55; 422/100; 422/58; 436/165; 436/180; 435/283.1; 435/287.1; 435/288.7; 435/288.3; 435/288.4

(58) Field of Classification Search ............. 435/283.1, 435/287.1, 288.7, 288.3, 288.4, 288.5; 422/102, 422/100, 55, 58; 436/165, 180
See application file for complete search history.

(56) References Cited

U.S. PATENT DOCUMENTS 5,229,297 A * 7/1993 Schnipelsky et al. ......... 436/94
6,284,531 B1 * 9/2001 Zhu et al. ................ 435/305.3
7,125,711 B2 * 10/2006 Pugia et al. ............. 435/288.5
2001/0048895 A1 * 12/2001 Virtanen .................... 422/68.1
2002/0123059 A1 * 9/2002 Ho ................................. 435/6
2003/0170881 A1 * 9/2003 Davis et al. ............. 435/287.2

* cited by examiner

*Primary Examiner*—Long V. Le
*Assistant Examiner*—Melanie J. Yu
(74) *Attorney, Agent, or Firm*—Troxell Law Office, PLLC

(57) ABSTRACT

An immunoassay cartridge for sensing at least one analyte in a biological sample is disclosed. The immunoassay cartridge comprises a supporting plate, a reaction cavity made within the supporting plate and having at least one analyte-binding molecule immobilized therein, a sample receiving end connected to the reaction cavity to allow the biological sample to flow into the reaction cavity for forming at least one complex of the analyte and the analyte-binding molecule, a first package containing a recognizing molecule, a first channel communicating the first package and the reaction cavity to allow the recognizing molecule to flow into the reaction cavity for forming a first product of the complex and the complex-binding molecule, a second package containing a buffer solution and a second channel communicating the second package and the reaction cavity to allow the buffer solution to flow into the reaction cavity.

7 Claims, 3 Drawing Sheets

IMMUNOASSAY DEVICES AND METHODS OF USING SAME

TECHNICAL FIELD OF THE INVENTION

The present invention relates to immunoassay devices and methods of using same. More particularly, the present invention relates to immunoassay devices capable of being accommodated by an analyzer for automatic immunoassays.

BACKGROUND OF THE INVENTION

Immunoassays using immobilized immunoreagents are in widespread use for the detection and quantification of biological molecules in samples. An immunoreagent, which may comprise an antibody or antigen, is first immobilized on a solid surface, such as a test tube, microplate, beads or the like. The immobilized reagent is then contacted with a sample solution containing a complementary immunoreagent, whereby an immobilized immunocomplex is formed between the immunoreagent and complementary immunoreagent. The immobilized immunocomplex can be separated from the unreacted sample solution, preferably with repeated washing of the immobilized immunocomplex. The separated immunocomplex may be subjected to further processing to quantitate the amount of the immunocomplex. Quantitative methods include, for example, radioimmunoassay (RIA), wherein the amount of the adsorbed immunocomplex may be determined by counting radioactive disintegrations; enzyme-linked immunosorbent assay (ELISA), wherein the adsorbed immunocomplex, which has an enzyme coupled thereto, is contacted with a substrate for the enzyme to produce a detectable product; immunofluorescent assay, wherein the fluorescent intensity of a fluorescent substance linked to the immunocomplex is measured; and chemiluminescent assay wherein the chemiluminescence of a chemiluminescent agent is measured.

Processes of the immunoassays, however, take time and resources. In addition, errors generated during the complex immunoassay accumulate gradually. For example, the enzymatic immunoassay is conducted by measuring the fluorescence intensity of the substrate after a certain period of time, either stopping the enzyme reaction with a stopping solution or not. In these steps, the duration from the initiation of enzyme reaction to the measurement should be strictly controlled, and so-called zero point correction is needed for the fluorescence intensity of the substrate because the intensity at the starting point is not always zero.

Except above descriptions, a researcher or an operator usually needs to load samples, pipette reagents or add a substrate into a test tube upon a bench, pour the liquid inside the test tube directly over the lab sink, and place the test tube into a machine, e.g. the ELISA reader, when the immunoassay has been initiated. Accordingly, it takes time and energy for the researcher or the operator to complete the assay. In addition, contaminations cannot effectively avoided as long as the assay is carried out by humans.

SUMMARY OF THE INVENTION

The present invention discloses immunoassay cartridges for automatically detecting at least one analyte in a biological sample. One of the immunoassay cartridges comprises a supporting plate, a reaction cavity made within the supporting plate and having at least one analyte-binding molecule immobilized therein, a sample receiving end connected to the reaction cavity to allow the biological sample to flow into the reaction cavity for forming at least one complex of the analyte and the analyte-binding molecule, a first package containing a recognizing molecule, a first channel communicating the first package and the reaction cavity to allow the recognizing molecule to flow into the reaction cavity for forming a first product of the complex and the complex-binding molecule, a second package containing a buffer solution and a second channel communicating the second package and the reaction cavity to allow the buffer solution to flow into the reaction cavity.

Another immunoassay cartridge comprises a tank for containing a buffer solution, a supporting plate covered onto the tank to form an enclosure, a reaction cavity made within the cover plate and having at least one analyte-binding molecule immobilized therein, a conduit communicating the tank and the reaction cavity to allow the buffer solution to spill into the reaction cavity, a sample loading chamber for receiving the biological sample, a first channel communicating the sample loading chamber and the reaction cavity to allow the biological sample to flow into the reaction cavity for forming at least one complex of the analyte and the analyte-binding molecule; a first package containing a recognizing molecule and a second channel communicating the first package and the reaction cavity to allow the recognizing molecule to flow into the reaction cavity for forming a first product of the complex and the recognizing molecule.

The present invention discloses an immunoassay cartridge for sensing at least one analyte in a biological sample. The cartridge comprises a tank for containing a buffer solution, a supporting plate covered onto the tank to form an enclosure, a reaction cavity made within the cover plate and having at least one analyte-binding molecule immobilized therein, a conduit communicating the tank and the reaction cavity to allow the buffer solution to spill into the reaction cavity, a sample loading chamber for receiving the biological sample, a first channel communicating the sample loading chamber an the reaction cavity to allow the biological sample to flow into the reaction cavity for forming at least one complex of the analyte and the analyte-binding molecule, a first package within the supporting plate containing a recognizing molecule and a second channel communicating the first package and the reaction cavity to allow the recognizing molecule to flow into the reaction cavity for forming a first product of the complex and the recognizing molecule.

EXAMPLES

Example 1

Figure 1:
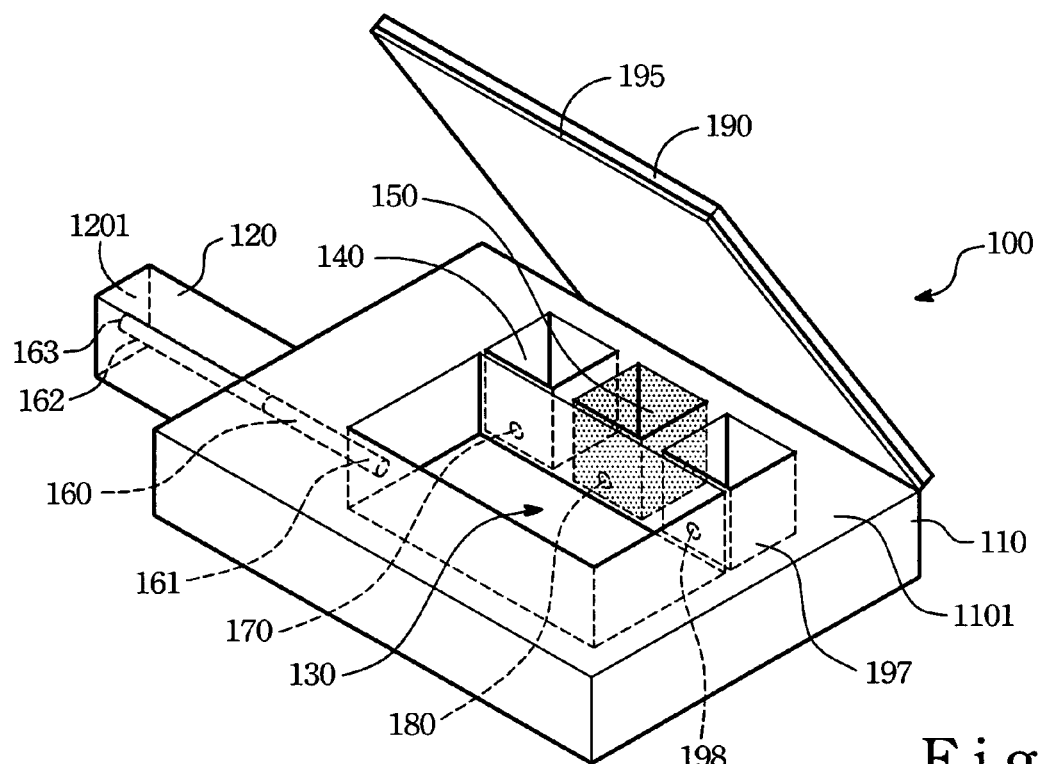
FIG. 1 shows a side view of an immunoassay cartridge according to the present invention.

Referring to FIG. 1, a side view of an immunoassay cartridge 100 is shown herein. The immunoassay cartridge 100 includes a plate structure 110 and an extending portion 120 coupled thereto. In an embodiment of the present invention, the extending portion 120 and the plate structure 110 are made by a procedure of one-piece molding. In another embodiment, the extending portion 120 and the plate structure 110 are fabricated separately and then assembled together.

Within the plate structure 110 includes a reaction cavity 130, and at least one analyte-binding molecule is immobilized on the bottom surface of the reaction cavity 130. In one preferred embodiment of the present invention, the analyte-binding molecule(s) within the reaction cavity 130 is/are printed to from an array. In addition, the method of immobilizing the analyte-binding molecule in the reaction cavity 130 comprises physical adsorption, cross-linking, covalent binding, entrapment or any combination thereof.

Methods of immobilization are described in detail below. However, it is appreciated that they are not used to limit the score and spirit of the present invention.

In one of these methods, a plateform made of poly (methylmethacrylate) (PMMA) is used as the bottom surface of the reaction cavity 130 and firstly derivatized by following a procedure similar to that described by Karandikar et al. at polym prepr 30:250-251 at 1989 with minor modifications. PMMA is well suited for use as a plateform for microfabricated devices because of its high dielectric constant, transparency, thermal conductivity that is comparable to silica, low cost, and ease of microfabrication.

Next, butyllithium (1 mmol) was transferred by cannula into a nitrogen-purged vessel containing 6 mmol of dry ethylenediamine or 1,3-diaminopropane. The resulting product of the addition of the ethylenediamine to butyllithium was dark purple, and upon addition of the 1,3-diaminopropane to butyllithium the product was yellowish-brown. After the reaction was stirred for 3 h, the lithiated diamine was added to a nitrogen-purged vessel containing the PMMA plateform to be derivatized. The reaction was quenched after 8 min with copious amounts of deionized water and the PMMA plateform were ready to be funtionalized.

The procedure for functionalization was similar to that of Locascio-Brown et al. published at Anal Chim Acta 228: 107-116 at 1990 with small adjustments. An aqueous solution of 5% (v/v) glutaric dialdehyde was added to the derivatized PMMA plateform and shaken for 4 h. Afterward the supernatant was discarded and the PMMA plateform were washed with deionized water several times. To immobilize the analyte-binding molecule, a reaction mixture containing the analyte-binding molecule, 50 mM Tris-HCl, 10 mM $MgCl_2$, 20% glycerol, and 50 mM sodium chloride was printed onto the bottom surface of the reaction cavity 130 and incubated for 3 h at 37° C. The reaction cavity 130 was then washed with 50 mM monobasic sodium phosphate buffer (may contain surfactant such as 0.5% Tween 20), deionized water, and stored in an appropriated buffer at 4° C. until use.

Another method of immobilizing the analyte-binding molecule on a silicate-based plateform is described. Firstly, the cleaned plateform was washed with sodium-dried toluene and then immersed in a solution of 10% 3-aminopropyltriethoxysilane (APTES) in dried toluene overnight at room temperature (RT). After removal of the solution, the plateform was rinsed several times with toluene and acetone and dried in an oven at 110° C. for 1 h. The dried plateform was immersed in 100 mL ethanol and sonicated for 10 min to introduce the solvent into the pores.

After washing with borate buffer (BB), the amine groups of the APTES silanized plateform was reacted with 2.5% v/v glutaraldehyde (GA) in BB for 1 h at RT, followed by thorough rinsing with deionized water in order to remove traces of glutaraldehyde to avoid cross-linking after addition of the analyte-binding molecule. Analyte-binding molecule (1 mg/mL) in BB was added to the GA-activated plateforms and reacted overnight at 4° C. under gentle shaking. After 12 h, the residual aldehyde groups remaining after analyte-binding molecule attachment were blocked with 10 mg/mL of L-lysine. The Schiff bases were reduced with 20 mg/mL $NaBH_3CN$ solution in BB, and the plateforms were allowed to proceed for 1-2 h under stirring at RT. The plateforms were then carefully washed and stored in 0.1 M Tris/HCl buffer at 4° C. until use.

For the silicate-based plateform, another method of immobilization is described herein. The cleaned microchips were immersed in 0.5% v/v solution of BPEI (branched polyethylenimine) in BB and kept under stirring at RT overnight and then thoroughly washed with BB. To incorporate active aldehyde groups, the plateform was reacted with 2.5% v/v GA in BB for 2 h at RT under stirring. After careful washing with deionized water and BB, the aldehyde-functionalized plateforms were printed with analyte-binding molecule solution at the concentration of 0.5 to 1 mg/mL for overnight at 4° C. Then residual aldehyde groups on the plateform were blocked and the Schiff bases reduced as described above.

Another method of immobilizing the analyte-binding molecule is described herein. The cleaned plateform was reacted with 3-glycidoxypropyltrimethoxysilane (GOPS) in dry toluene, containing 2% v/v GOPS and 0.2% triethylamine at RT. After 1 h, the GOPS-coated plateform was first rinsed with toluene, then with acetone, and then dried in an oven at 110° C. for 1 h. To introduce a solvent in the pores, the plateform was sonicated in 100 mL of ethanol for 10 min and then were washed with deionized water. A solution of 0.5% v/v BPEI in succinate buffer was added, and the reaction mixture was gently shaken for 5 h at RT. After careful washing with deionized water, the plateform was treated with 2.5% v/v GA in BB. After 2 h, the microchips were rinsed and then immersed in analyte-binding molecule solution in BB with the concentration of 0.5 to 1 mg/mL. The reaction was allowed to proceed overnight at 4° C., after which the plateform was blocked and reduced as described above.

Still another method of immobilization is described herein. Two approaches were used to immobilize the analyte-binding molecule on to the surfaces of the PDMS plateform: namely, (1) passive adsorption on the surface; and (2) site-selective binding to immobilized analyte-binding molecule. In the first approach, 10 mg/ml of analyte-binding molecules were passively adsorbed on to the surfaces of the PDMS plateform from a 0.1 M PBS buffer solution (pH 7.4) for 90 min. This was followed by a blocking step for 1 h. The composition of the blocking buffer used was 0.5% BSA (w/v), 0.5% casein (w/v) and 0.5% Tween 20 (v/v) in PBS. In the second approach, PDMS plateform was functionalized with analyte-binding molecule in the following three-step process: first, the surface was coated with BSA (1 mg/ml in sodium phosphate buffer) for 3.5 h. Second, the BSA-coated surface was then activated with 0.1% GA in pure water for 1 h. Finally, analyte-binding molecule (20 mg/ml in sodium phosphate buffer) was covalently bound via the GA groups. No blocking step was used following the attachment of the capture antibody molecules. All experiments were carried out at room temperature.

One end 161 of a sample receiving end 160 is connected to the reaction cavity 130. The other end 162 of the sample receiving end 160 penetrates through the extending portion 120 and has an opening 163 on a sidewall 1201 of the extending portion 120. In this embodiment, the extending portion 120 is provided to protect the sample receiving end 160 from being broken.

A biological sample suspected of an analyte is received from the opening 163 and flows into the reaction cavity 130 via the sample receiving end 160. In another embodiment, the biological sample is loaded into the reaction cavity 130. That is, the sample receiving end 160 can be optionally omitted from the immunoassay cartridge 100 according to practical needs. The biological sample preferably comprises a blood sample, a serum sample or a saliva sample. In addition, the sample receiving end 160 is a capillary.

In one preferred embodiment of the present invention, the analyte is an antigen and the analyte-binding molecule is a first antibody correspondingly. In another embodiment, the analyte-binding molecule is a ligand when the analyte is a protein.

The plate structure 110 comprises a first package 140 and a second package 150 filled with a recognizing molecule and a buffer solution, respectively. It is noted that the recognizing molecule is preferably a second antibody when the analyte is the antigen and the analyte-binding molecule is the first antibody. However, it is appreciated that these are not used to limit the score and the spirit of the present invention.

As shown in the figure, both of the first package 140 and the second package 150 are adjacent to the reaction cavity 130. A first channel 170 is used to communicate the first package 140 and reaction cavity 130, whereas a second channel 180 is used to communicate the second package 150 and reaction cavity 130.

In one preferred embodiment of the present invention, the first package 140 and the second package 150 comprise pits fabricated within the plate structure 110 and coverings covered onto the pits. In another embodiment, the first package 140 and the second package 150 comprise containers coupled to the plate structure 110 and coverings covered onto the containers.

The first channel 170 and the second channel 180 are both sealed by stoppers. When the covering of the first package 140 or the second package 150 is pressurized, the recognizing molecule or the buffer solution inside the respective first package 140 or the second package 150 breaks through the stopper and flows into the reaction cavity 130. In the embodiment, the covering is made of polymer such as PDMS or PET (polyethylene terephthalate). The stopper could be made of a wide variety of materials including silicon, polyvinyl alcohol (PVA), polystyrene (PS) or other polymers.

The immunoassay cartridge 100 further comprises a removable lid 190 capable of being covered onto the plate structure 110. On the inner surface of the removable lid 190 is lined with an adsorption pad 195. In one preferred embodiment of the present invention, the adsorption pad 195 is made of adsorbing materials like membranes, tissues, or polymers such as starch-acrylic acid graft copolymer, copoly (vinyl alchol-acrylic acid), cross-linking copolyacrylic acid or combinations thereof. It is appreciated that these are not used to limit the score and the spirit of the present invention.

When the immunoassay cartridge 100 is accommodated by an analyzer (not shown herein), the biological sample flowing into the reaction cavity 130 through the sample receiving end 160 reacts with the analyte-binding molecule immobilized in the reaction cavity 130, thus forming a complex of the analyte and the analyte-binding molecule.

Thereafter, the removable lid 190 is covered onto the plate structure 110 to allow the adsorption pad 195 attached thereinside to adsorb the liquid in the reaction cavity 130. Next, the removable lid 190 is lifted to leave the plate structure 110.

It is noted that the coverings of the first package 140 and the second package 150 should be avoided swelling out of the upper surface 1101 of the plate structure 110 when the first package 140 and the second package 150 are loaded with the recognizing molecule and the buffer solution. Accordingly, the recognizing molecule and the buffer solution inside the first package 140 and the second package 150 will not be squeezed into the reaction cavity 130 while covering the removable lid 190 onto the plate structure 110.

After forming the complex of the analyte and the analyte-binding molecule, the buffer solution in the second package 150 is automatically pressed to break the stopper and flow into the reaction cavity 130 via the second channel 180 for a purpose of wash.

Next, the used adsorption pad 195 should be replaced with a fresh one by the analyzer for avoiding contaminations. That is, the used adsorption pad 195 should be replaced with a fresh one every time when it is used to adsorb the liquid within the reaction cavity 130.

After that, the removable lid 190 is covered to the plate structure 110 to allow the new adsorption pad 195 attached thereinside to adsorb the liquid in the reaction cavity 130.

In another embodiment, the adsorption pad 195 is directly installed in the analyzer instead of being attached on the removable lid 190. The purpose of the adsorption pad 195 is to adsorb the liquid within the reaction cavity 130 rapidly. Accordingly, various possible modifications and substitutions, without departing from the purpose, should be included in the present invention. After evacuating the liquid within the reaction cavity 130 using the adsorption pad 195, the removable lid 190 is removed from the plate structure 110.

Next, the recognizing molecule such as a gold-conjugated antibody in the first package 140 is automatically forced to break the stopper and flow into the reaction cavity 130 via the first channel 170, thus forming a first product of the complex and the recognizing molecule. After that, the removable lid 190 is covered to the plate structure 110 to allow the adsorption pad 195 attached thereinside to adsorb the liquid in the reaction cavity 130. The removable lid 190 is then removed from the plate structure 110. Lastly, the second package 150 is automatically pressed again to force the buffer solution to flow into the reaction cavity 130 for rinse.

It is noted that, in another embodiment, diameters of the first channel 170 and the second channel 180 are designed to allow the recognizing molecule and the buffer solution to stay in the first package 140 and the second package 150 and then flow into the reaction cavity 130 when the first package 140 and the second package 150 suffer the pressure. That is, the stopper described above is absent in this embodiment.

The plate structure 110 in this example optionally comprises a third package 197 filled with a signal molecule. In one preferred embodiment of the present invention, the third package 197 comprises a pit made within the plate structure 110 and a covering covered onto the pit. In another embodiment, the third package 197 comprises a container coupled to the plate structure 110 and a covering covered onto the container.

In the enzymatic immunoassay, the complex of the analyte and the analyte-binding molecule is bound with an enzyme. The enzyme-bound complex is then contacted with the signal molecule, e.g. a substrate, for the enzyme to produce a detectable substance.

As described above, a third channel 198 communicates the third package 197 and the reaction cavity 130. Accordingly, the third package 197 is adjacent to the reaction cavity 130.

In one preferred embodiment of the present invention, the third package 197 comprises a pit fabricated within the plate structure 110 and a covering covered onto the pit. Further, the third channel 198 is sealed by a stopper. When the covering of the third package 197 is pressurized, the signal molecule inside the third package 197 breaks through the stopper and flows into the reaction cavity 130. The covering is preferably made of polymer such as PDMS or PET (polyethylene terephthalate). The stopper is made of a wide variety of materials including silicon, polyvinyl alcohol (PVA), polystyrene (PS) or other polymers.

After forming the first product of the complex and the recognizing molecule and washing the reaction cavity 130 with the buffer solution, the signal molecule in the third package 197 is automatically pressed to break the stopper and flow into the reaction cavity 130 via the third channel 198, thus forming a second product of the first product and the signal molecule. Subsequently, the removable lid 190 is covered to the plate structure 110 to allow the adsorption pad 195 attached thereinside to adsorb the liquid in the reaction cavity 130. Then, the removable lid 190 is removed from the plate structure 110.

Lastly, the second package 150 is automatically pressed again to force the buffer solution to flow into the reaction cavity 130 for rinse. The second product is subjected to detect the concentration of the analyte in the biological sample.

It is noted that, in another embodiment, a diameter of the third channel 198 is designed to allow the signal molecule to stay in the third package 197 and then flow into the reaction cavity 130 when the third package 197 is pressed. In other words, the stopper described above is absent herein.

Example 2

Figure 2:
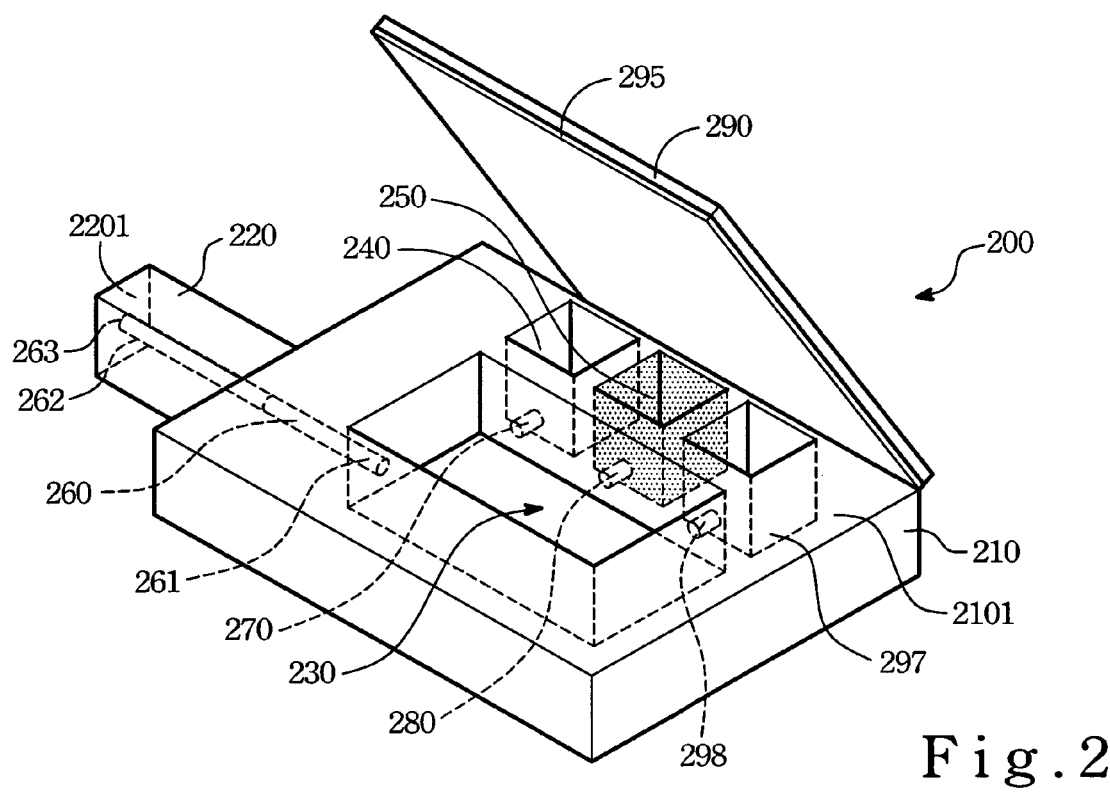
FIG. 2 shows a side view of an immunoassay cartridge according to the present invention.

Referring to FIG. 2, a side view of an immunoassay cartridge 200 is shown herein. The immunoassay cartridge 200 includes a plate structure 210 and an extending portion 220 coupled thereto. In an embodiment of the present invention, the extending portion 220 and the plate structure 210 are made by a procedure of one-piece molding. In another embodiment, the extending portion 220 and the plate structure 210 are fabricated separately and then assembled together.

Within the plate structure 210 includes a reaction cavity 230, and at least one analyte-binding molecule is immobilized on the bottom surface of the reaction cavity 230. In a preferred embodiment of the present invention, the analyte-binding molecule(s) within the reaction cavity 230 is/are printed as an array. In addition, the method of immobilizing the analyte-binding molecule in the reaction cavity 230 comprises physical adsorption, cross-linking, covalent binding, entrapment or any combination thereof.

One end 261 of a sample receiving end 260 is connected to the reaction cavity 230. The other end 262 of the sample receiving end 260 penetrates through the extending portion 220 and has an opening 263 on a sidewall 2201 of the extending portion 220. In this embodiment, the extending portion 220 is provided to protect the sample receiving end 260 from being broken.

A biological sample suspected of an analyte is received from the opening 263 and flows into the reaction cavity 230 via the sample receiving end 260. In another embodiment, the biological sample is loaded into the reaction cavity 230. That is, the sample receiving end 260 can be optionally omitted from the immunoassay cartridge 200 according to practical needs.

The biological sample preferably comprises a blood sample, a serum sample or a saliva sample. In addition, the sample receiving end 260 is a capillary.

In one preferred embodiment of the present invention, the analyte is an antigen and the analyte-binding molecule is a first antibody correspondingly. In another embodiment, the analyte-binding molecule is a ligand when the analyte is a protein.

The plate structure 210 comprises a first package 240 and a second package 250 filled with a recognizing molecule and a buffer solution, respectively. It is noted that the recognizing molecule is preferably a second antibody when the analyte is the antigen and the analyte-binding molecule is the antigen. However, it is appreciated that these are not used to limit the score and the spirit of the present invention.

Differences between Example 1 and Example 2 are that the immunoassay cartridge 200 in this example further comprises a first pipe 270 and a second pipe 280. The first pipe 270 is used to communicate the first package 240 and reaction cavity 230, whereas the second pipe 280 is served to connect the second package 250 and reaction cavity 230. As shown in the figure, the first pipe 270 and the second pipe 280 are embedded within the plate structure 210. It is appreciated that, however, this is not used to limit the score and the spirit of the present invention.

In one preferred embodiment of the present invention, the first package 240 and the second package 250 comprise pits fabricated within the plate structure 210 and coverings covered onto the pits. In another embodiment, the first package 240 and the second package 250 comprise containers coupled to the plate structure 210 and coverings covered onto the containers.

The first pipe 270 and the second pipe 280 are both sealed by stoppers. When the covering of the first package 240 or the second package 250 is pressurized, the recognizing molecule or the buffer solution inside the respective first package 240 or the second package 250 breaks through the stopper and flows into the reaction cavity 230. The covering is preferably made of polymer such as PDMS or PET (polyethylene terephthalate). The stopper is made of a wide variety of materials including silicon, polyvinyl alcohol (PVA), polystyrene (PS) or other polymers.

As described in Example 1, the immunoassay cartridge 200 in this example also comprises a removable lid 290 capable of being covered onto the plate structure 210. On the inner surface of the removable lid 290 is lined with an adsorption pad 295. In one preferred embodiment of the present invention, the adsorption pad 295 is made of adsorbing materials like membranes, tissues, or polymers such as starch-acrylic acid graft copolymer, copoly (vinyl alchol-acrylic acid), cross-linking copolyacrylic acid or combinations thereof. It is appreciated that these are not used to limit the score and the spirit of the present invention.

When the immunoassay cartridge 200 is accommodated by an analyzer (not shown herein), the biological sample flowing into the reaction cavity 230 through the sample receiving end 260 reacts with the analyte-binding molecule immobilized in the reaction cavity 230, thus forming a complex of the analyte and the analyte-binding molecule.

Thereafter, the removable lid 290 is covered onto the plate structure 210 to allow the adsorption pad 295 attached thereinside to adsorb the liquid in the reaction cavity 230. Next, the removable lid 290 is removed from the plate structure 210.

It is noted that the coverings of the first package 240 and the second package 250 should be avoided swelling out of the upper surface 2101 of the plate structure 210 when the first package 240 and the second package 250 are loaded with the recognizing molecule and the buffer solution. Accordingly, the recognizing molecule and the buffer solution inside the first package 240 and the second package 250 will not be squeezed into the reaction cavity 230 while covering the removable lid 290 onto the plate structure 210.

After forming the complex of the analyte and the analyte-binding molecule, the buffer solution in the second package 250 is automatically pressed to break the stopper and flow into the reaction cavity 230 via the second pipe 280 for wash. Next, the used adsorption pad 295 should be replaced with a fresh one by the analyzer for avoiding contaminations. That is, the used adsorption pad 295 should be replaced with a fresh one every time when it is used to adsorb the liquid within the reaction cavity 230.

After that, the removable lid 290 is covered to the plate structure 210 to allow the new adsorption pad 295 attached thereinside to adsorb the liquid in the reaction cavity 230.

In another embodiment, the adsorption pad 295 is directly installed in the analyzer instead of being attached on the removable lid 290. The purpose of the adsorption pad 295 is to adsorb the liquid within the reaction cavity 230 rapidly. Accordingly, various possible modifications and substitutions, without departing from the purpose, should be should be included in the present invention. After evacuating the liquid within the reaction cavity 230 using the adsorption pad 295, the removable lid 290 is removed from the plate structure 210.

Next, the recognizing molecule such as a gold-conjugated antibody in the first package 240 is automatically squeezed to break the stopper and flow into the reaction cavity 230 via the first pipe 270, thus forming a first product of the complex and the recognizing molecule. After that, the removable lid 290 is covered onto the plate structure 210 to allow the adsorption pad 295 attached thereinside to adsorb the liquid contained in the reaction cavity 230. The removable lid 290 is then removed from the plate structure 210. Lastly, the second package 250 is automatically pressed again to force the buffer solution to flow into the reaction cavity 230 for rinse.

It is noted that, in another embodiment, diameters of the first channel 270 and the second channel 280 are designed to allow the recognizing molecule and the buffer solution to stay in the first package 240 and the second package 250 and then flow into the reaction cavity 230 when the first package 240 and the second package 250 suffer the pressure. That is, the stopper described above is absent in this embodiment.

In one preferred embodiment of the present invention, the third package 297 comprises a pit made within the plate structure 210 and a covering covered onto the pit. In another embodiment, the third package 297 comprises a container coupled to the plate structure 210 and a covering covered onto the container.

In the enzymatic immunoassay, the complex of the analyte and the analyte-binding molecule is bound with an enzyme. The enzyme-bound complex is then contacted with the signal molecule, e.g. a substrate, for the enzyme to produce a detectable substance.

As described above, a third pipe 298 communicates the third package 297 and the reaction cavity 230. Accordingly, the third package 297 is adjacent to the reaction cavity 230.

In one preferred embodiment of the present invention, the third package 297 comprises a pit fabricated within the plate structure 210 and a covering covered onto the pit. Further, the third channel 298 is sealed by a stopper. When the covering of the third package 297 is pressurized, the signal molecule inside the third package 297 breaks through the stopper and flows into the reaction cavity 230. The covering is preferably made of polymer such as PDMS or PET (polyethylene terephthalate). The stopper is made of a wide variety of materials including silicon, polyvinyl alcohol (PVA), polystyrene (PS) or other polymers. In another embodiment, the third package 297 is coupled to the plate structure 210.

After forming the first product of the complex and the recognizing molecule and washing the reaction cavity 230 with the buffer solution, the signal molecule in the third package 297 is automatically pressed to break the stopper and flow into the reaction cavity 230 via the third channel 298, thus forming a second product of the first product and the signal molecule. Subsequently, the removable lid 290 is covered to the plate structure 210 to allow the adsorption pad 295 attached thereinside to adsorb the liquid in the reaction cavity 230. Then, the removable lid 290 is removed from the plate structure 210.

Lastly, the second package 250 is automatically pressed again to force the buffer solution to flow into the reaction cavity 230 for rinse. The second product is subjected to detect the concentration of the analyte in the biological sample.

It is noted that, in another embodiment, a diameter of the third channel 298 is designed to allow the signal molecule to stay in the third package 297 and then flow into the reaction cavity 230 when the third package 297 is pressed. In other words, the stopper described above is absent herein.

Example 3

Figure 3:
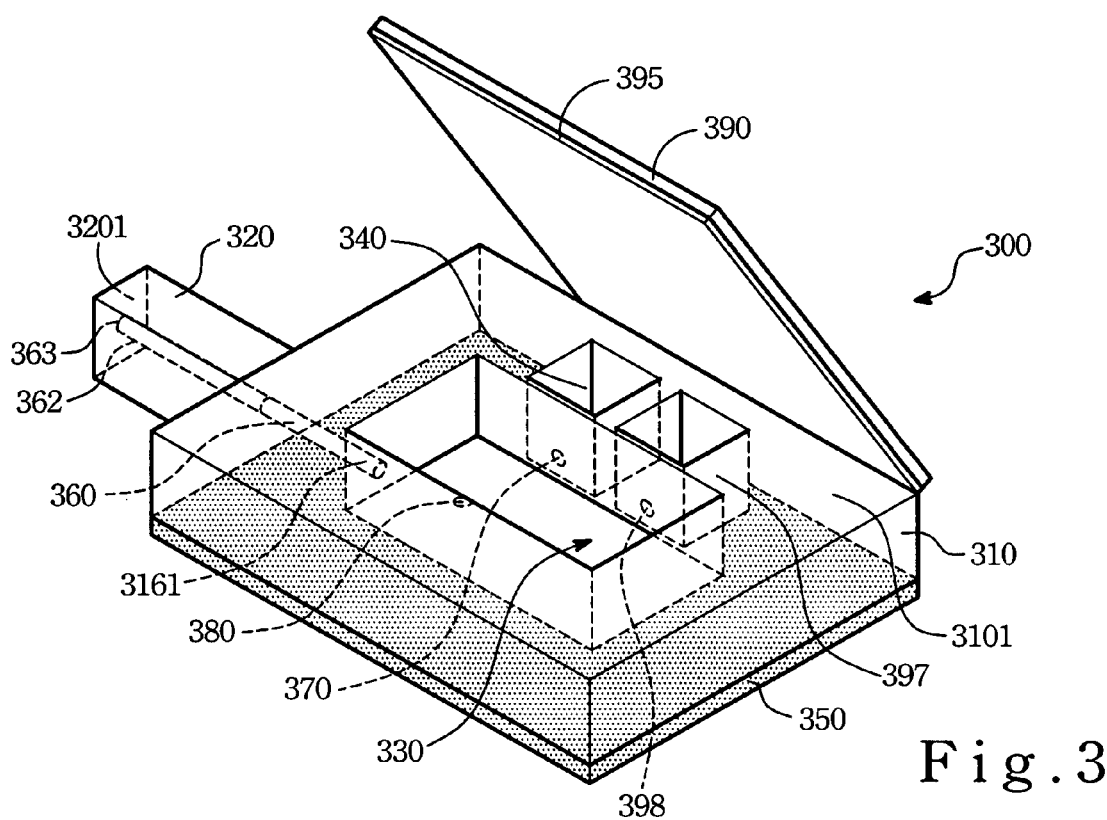
FIG. 3 shows a side view of an immunoassay cartridge according to the present invention.

Referring to FIG. 3, a side view of an immunoassay cartridge 300 is shown herein. The immunoassay cartridge 300 includes a plate structure 310 and an extending portion 320 coupled thereto. In an embodiment of the present invention, the extending portion 320 and the plate structure 310 are made by a procedure of one-piece molding. In another embodiment, the extending portion 320 and the plate structure 310 are fabricated separately and then assembled together.

Within the plate structure 310 includes a reaction cavity 330, and at least one analyte-binding molecule is immobilized on the bottom surface of the reaction cavity 330. In one preferred embodiment of the present invention, the analyte-binding molecule(s) within the reaction cavity 330 is/are printed to form an array. In addition, the method of immobilizing the analyte-binding molecule in the reaction cavity 330 comprises physical adsorption, cross-linking, covalent binding, entrapment or any combination thereof.

One end 361 of a sample receiving end 360 is connected to the reaction cavity 330. The other end 362 of the sample receiving end 360 penetrates through the extending portion 320 and has an opening 363 on a sidewall 3201 of the extending portion 320. In this embodiment, the extending portion 320 is provided to protect the sample receiving end 360 from being broken.

A biological sample suspected of an analyte is received from the opening 363 and flows into the reaction cavity 330 via the sample receiving end 360. In another embodiment, the biological sample is loaded into the reaction cavity 330. That is, the sample receiving end 360 can be optionally omitted from the immunoassay cartridge 300 according to practical needs.

The biological sample preferably comprises a blood sample, a serum sample or a saliva sample. In addition, the sample receiving end 360 is a capillary.

In one preferred embodiment of the present invention, the analyte is an antigen and the analyte-binding molecule is a first antibody correspondingly. In another embodiment, the analyte-binding molecule is a ligand when the analyte is a protein.

The immunoassay cartridge 300 further comprises a first package 340 within the plate structure 310 and a second package 350 under the plate structure 310. The first package 340 is filled with a recognizing molecule, and the second package 350 is full of a buffer solution. In another embodiment, the first package 340 comprises a container coupled to the plate structure 310 and a covering covered onto the container.

The recognizing molecule is preferably a second antibody when the analyte is the antigen and the analyte-binding molecule is the first antibody. However, it is appreciated that these are not used to limit the score and the spirit of the present invention. One of differences between Example 3 and Example 1 is that the second package 350 in this example is located under the plate structure 310.

A first channel 370 within the plate structure 310 communicates the first package 340 and reaction cavity 330, whereas a second channel 380 connects the second package 350 and reaction cavity 330. A diameter of the second channel 380 is designed to avoid the liquid within the reaction cavity 330 leaking to the second package 350.

In one preferred embodiment of the present invention, the first package 340 comprises a pit fabricated within the plate structure 310 and a covering covered thereonto. In addition, the first channel 370 and the second channel 380 are both sealed by stoppers. When the covering of the first package 340 is pressed, the recognizing molecule contained therein breaks through the stopper and flows into the reaction cavity 330. When the second package 350 is pressurized, the buffer solution contained therein breaks through the stopper and spills into the reaction cavity 330. The covering is preferably made of polymer such as PDMS or PET (polyethylene terephthalate). The stopper is made of a wide variety of materials including silicon, polyvinyl alcohol (PVA), polystyrene (PS) or other polymers.

As described in Example 1, the immunoassay cartridge 300 in this example further comprises a removable lid 390 capable of being covered onto the plate structure 310. On the inner surface of the removable lid 390 is lined with an adsorption pad 395. In one preferred embodiment of the present invention, the adsorption pad 395 is made of adsorbing materials like membranes, tissues, or polymers such as starch-acrylic acid graft copolymer, copoly (vinyl alcholacrylic acid), cross-linking copolyacrylic acid or combinations thereof. It is appreciated that these are not used to limit the score and the spirit of the present invention.

When the immunoassay cartridge 300 is accommodated by an analyzer (not shown herein), the biological sample flowing into the reaction cavity 330 through the sample receiving end 360 reacts with the analyte-binding molecule immobilized in the reaction cavity 330, thus forming a complex of the analyte and the analyte-binding molecule.

Thereafter, the removable lid 390 is covered onto the plate structure 310 to allow the adsorption pad 395 attached thereinside to adsorb the liquid in the reaction cavity 330. Next, the removable lid 390 is removed from the plate structure 310.

It is noted that the covering of the first package 340 should be avoided swelling out of the upper surface 3101 of the plate structure 310 when the first package 340 is loaded with the recognizing molecule. Accordingly, the recognizing molecule contained in the first package 340 will not be squeezed into the reaction cavity 330 while covering the removable lid 390 onto the plate structure 310.

After forming the complex of the analyte and the analyte-binding molecule, the second package 350 is automatically compressed to have the buffer solution therein break the stopper and spill into the reaction cavity 330 via the second channel 380 for wash. Next, the used adsorption pad 395 should be replaced with a fresh one by the analyzer for avoiding contaminations. That is, the used adsorption pad 395 should be replaced with a fresh one every time when it is used to adsorb the liquid within the reaction cavity 330.

After that, the removable lid 390 is covered to the plate structure 310 to allow the new adsorption pad 395 attached thereinside to adsorb the liquid in the reaction cavity 330.

In another embodiment, the adsorption pad 395 is directly installed in the analyzer instead of being attached on the removable lid 390. The purpose of the adsorption pad 395 is to adsorb the liquid within the reaction cavity 330 rapidly. Accordingly, various possible modifications and substitutions, without departing from the purpose, should be should be included in the present invention. After evacuating the liquid within the reaction cavity 330 using the adsorption pad 395, the removable lid 390 is removed from the plate structure 310.

Next, the recognizing molecule such as a gold-conjugated antibody in the first package 340 is automatically squeezed to break the stopper and flow into the reaction cavity 330 via the first channel 370, thus forming a first product of the complex and the recognizing molecule. After that, the removable lid 390 is covered onto the plate structure 310 to allow the adsorption pad 395 attached thereinside to adsorb the liquid contained in the reaction cavity 330. The removable lid 390 is then removed from the plate structure 310. Lastly, the second package 350 is automatically compressed again to force the buffer solution to spill into the reaction cavity 330 for rinse.

It is noted that, in another embodiment, diameters of the first channel 370 and the second channel 380 are designed to allow the recognizing molecule and the buffer solution to stay in the first package 340 and the second package 350 and then flow into the reaction cavity 330 when the first package 340 and the second package 350 suffer the pressure. That is, the stopper described above is absent in this embodiment.

In one preferred embodiment of the present invention, the third package 397 comprises a pit made within the plate structure 330 and a covering covered onto the pit. In another embodiment, the third package 397 comprises a container coupled to the plate structure 330 and a covering covered onto the container.

In the enzymatic immunoassay, the complex of the analyte and the analyte-binding molecule is bound with an enzyme. The enzyme-bound complex is then contacted with the signal molecule, e.g. a substrate, for the enzyme to produce a detectable substance.

As described above, a third channel 398 communicates the third package 397 and the reaction cavity 330. Accordingly, the third package 397 is adjacent to the reaction cavity 330.

In one preferred embodiment of the present invention, the third package 397 comprises a pit fabricated within the plate structure 310 and a covering covered onto the pit. Further, the third channel 398 is sealed by a stopper. When the covering of the third package 397 is pressurized, the signal molecule inside the third package 397 breaks through the stopper and flows into the reaction cavity 330. The covering is preferably made of polymer such as PDMS or PET (polyethylene terephthalate). The stopper is made of a wide variety of materials including silicon, polyvinyl alcohol (PVA), polystyrene (PS) or other polymers.

After forming the first product of the complex and the recognizing molecule and washing the reaction cavity 330 with the buffer solution, the signal molecule in the third package 397 is automatically pressed to break the stopper and flow into the reaction cavity 330 via the third channel 398, thus forming a second product of the first product and the signal molecule. Subsequently, the removable lid 390 is covered to the plate structure 310 to allow the adsorption pad 395 attached thereinside to adsorb the liquid in the reaction cavity 330. Then, the removable lid 390 is removed from the plate structure 310.

Lastly, the second package 350 is automatically pressed again to force the buffer solution to flow into the reaction cavity 330 for rinse. The second product is subjected to detect the concentration of the analyte in the biological sample.

It is noted that, in another embodiment, a diameter of the third channel 398 is designed to allow the signal molecule to stay in the third package 397 and then flow into the reaction cavity 330 when the third package 397 is pressed. In other words, the stopper described above is absent herein.

Example 4

Figure 4:
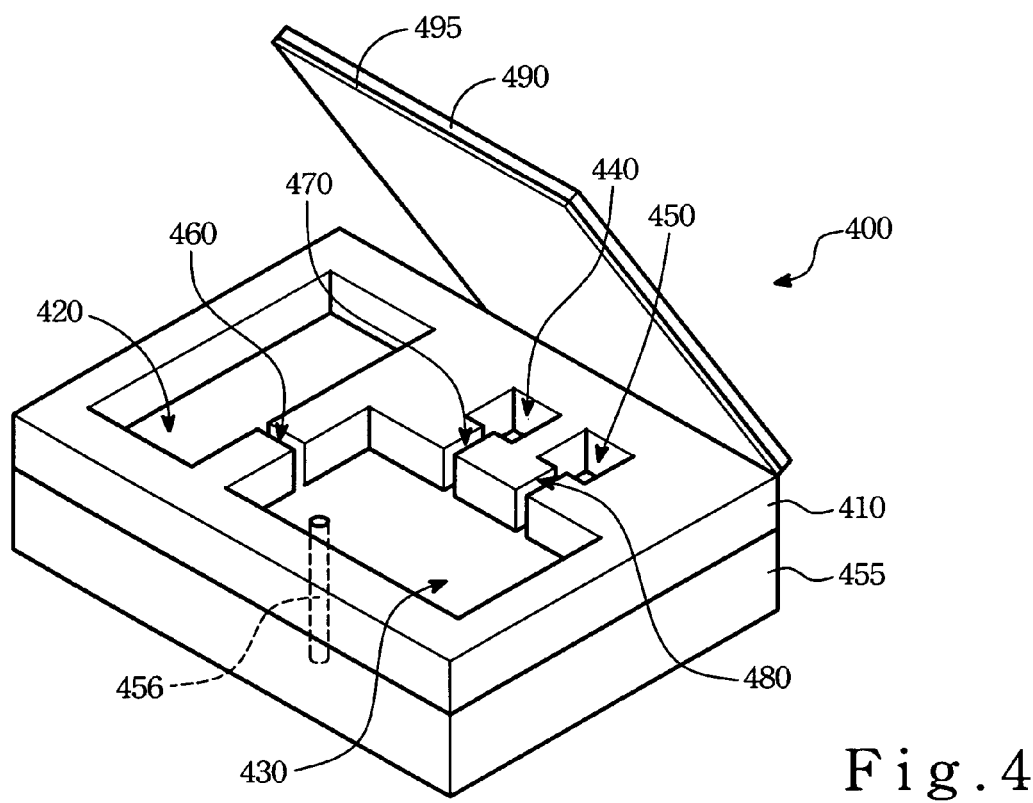
FIG. 4 shows a side view of an immunoassay cartridge according to the present invention.

Referring to FIG. 4, a side view of an immunoassay cartridge 400 is shown herein. The immunoassay cartridge 400 includes a supporting plate 410. A sample loading chamber 420 is fabricated within the supporting plate 410 and provided for receiving and containing a biological sample suspected of an analyte. In one preferred embodiment of the present invention, the biological sample comprises a blood sample, a serum sample or a saliva sample.

It is noted that the sample loading chamber 420 can be omitted optionally according to practical needs. In this case, the biological sample is loaded in the reaction cavity 430 directly.

Within the supporting plate 410 also includes a reaction cavity 430. At least one analyte-binding molecule is immobilized on the bottom surface of the reaction cavity 430. In one preferred embodiment of the present invention, the analyte-binding molecule(s) in the reaction cavity 430 is/are printed to from an array. The method of immobilizing the analyte-binding molecule within the reaction cavity 430 comprises physical adsorption, cross-linking, covalent binding, entrapment or any combination thereof.

In one preferred embodiment of the present invention, the analyte is an antigen and the analyte-binding molecule is a first antibody correspondingly. In another embodiment, the analyte-binding molecule is a ligand when the analyte is a protein.

Still referring to FIG. 4, a first channel 460 connects the sample loading chamber 420 and the reaction cavity 430 to allow the biological sample in the sample loading chamber 420 to flow into the reaction cavity 430.

The immunoassay cartridge 400 further comprises a first package 440 and a second package 450 filled with a recognizing molecule and a signal molecule, respectively. It is noted that the recognizing molecule is preferably a second antibody such as a gold-conjugated antibody, and the signal molecule is preferably a substrate while the analyte is the antigen and the analyte-binding molecule is the first antibody. However, it is appreciated that these are not used to limit the score and the spirit of the present invention.

As shown in the figure, a second channel 470 is used to communicate the first package 440 and the reaction cavity 430, whereas the third channel 480 is used to communicate the second package 450 and the reaction cavity 430. The supporting plate 410 is covered onto a tank 455 full of a buffer solution to form an enclosure. A conduit 456 connects the tank 455 and the reaction cavity 430 for allowing the buffer solution in the tank 455 to spill into the reaction cavity 430.

In one preferred embodiment of the present invention, the first package 440 and the second package 450 comprise pits fabricated within the supporting plate 410 and coverings covered onto the pits. In another embodiment, the first package 440 and the second package 450 comprise containers coupled to the enclosure and coverings covered onto the containers.

The second channel 470 and the third channel 480 are both sealed by stoppers. When the covering of the first package 440 or the second package 450 is pressed, the recognizing molecule or the substrate inside the respective first package 440 and the second package 450 breaks through the stopper and flows into the reaction cavity 430. In the embodiment, the covering is preferably made of polymer such as PDMS or PET (polyethylene terephthalate). The stopper is made of a wide variety of materials including silicon, polyvinyl alcohol (PVA), polystyrene (PS) or other polymers.

In another embodiment, diameters of the second channel 470 and the third channel 480 are designed to allow the recognizing molecule and the substrate to stay in the first package 440 and the second package 450 and then flow into the reaction cavity 430 when they are pressurized. That is, the stopper described above is absent in this embodiment.

It is noted that the first channel 460, the second channel 470 and the third channel 480 are not used to limit the score and the spirit of the present invention. That is, the first channel 460, the second channel 470 and the third channel 480 can be replaced with pipes or the like.

The immunoassay cartridge 400 further comprises a removable lid 490 capable of being covered onto the supporting plate 410. On the inner surface of the removable lid 490 is lined with an adsorption pad 495. In one preferred embodiment of the present invention, the adsorption pad 495 is made of adsorbing materials like membranes, tissues, or polymers such as starch-acrylic acid graft copolymer, copoly (vinyl alchol-acrylic acid), cross-linking copolyacrylic acid or combinations thereof. It is appreciated that these are not used to limit the score and the spirit of the present invention.

When the immunoassay cartridge 400 is accommodated by an analyzer (not shown herein), the biological sample flowing into the reaction cavity 430 through the first channel 460 reacts with the analyte-binding molecule immobilized in the reaction cavity 430, thus forming a complex of the analyte and the analyte-binding molecule.

Thereafter, the removable lid 490 is covered onto the supporting plate 410 to allow the adsorption pad 495 attached thereinside to adsorb the liquid in the reaction cavity 430. Next, the removable lid 490 is removed from the supporting plate 410.

It is noted that the covering of the first package 440 should be avoided swelling out of the upper surface 4101 of the supporting plate 410 when the first package 440 is loaded with the recognizing molecule. Accordingly, the recognizing molecule contained in the first package 440 will not be squeezed into the reaction cavity 430 while covering the removable lid 490 onto the plate structure 310.

After forming the complex of the analyte and the analyte-binding molecule, the buffer solution in the tank 455 is pressurized to spill into the reaction cavity 430 via the conduit 456 for wash. In the example, the buffer solution in the tank 455 is pumped to the reaction cavity 430 via the conduit 456.

Next, the used adsorption pad 495 should be replaced with a fresh one by the analyzer for avoiding contaminations. That is, the used adsorption pad 495 should be replaced with a fresh one every time when it is used to adsorb the liquid within the reaction cavity 430.

Thereafter, the removable lid 490 is covered to the supporting plate 410 to allow the new adsorption pad 495 attached thereinside to adsorb the liquid in the reaction cavity 430.

In another embodiment, the adsorption pad 495 is directly installed in the analyzer instead of being attached on the removable lid 490. The purpose of the adsorption pad 495 is to adsorb the liquid within the reaction cavity 430 rapidly. Accordingly, various possible modifications and substitutions, without departing from the purpose, should be should be included in the present invention. After evacuating the liquid within the reaction cavity 430 using the adsorption pad 495, the removable lid 490 is removed from the supporting plate 410.

Next, the recognizing molecule such as a gold-conjugated antibody in the first package 440 is automatically squeezed to break the stopper and flow into the reaction cavity 430 via the second channel 470, thus forming a first product of the complex and the recognizing molecule. After that, the removable lid 490 is covered onto the supporting plate 410 to allow the adsorption pad 495 attached thereinside to adsorb the liquid contained in the reaction cavity 430. The removable lid 490 is then removed from the plate structure 410.

After forming the first product of the complex and the recognizing molecule, the buffer solution in the tank 455 is automatically pressurized to spill into the reaction cavity 430 via the conduit 456 for rinse. Then, the removable lid 490 is covered onto the supporting plate 410 to allow the adsorption pad 495 attached thereinside to adsorb the liquid in the reaction cavity 430. Thereafter, the removable lid 490 is removed from the supporting plate 410.

Next, the signal molecule in the second package 450 is automatically squeezed to break the stopper and flow into the reaction cavity 430 via the third channel 480, thus forming a second product of the intermediate and the signal molecule. After that, the removable lid 490 is covered onto the supporting plate 410 to allow the adsorption pad 495 attached thereinside to adsorb the liquid contained in the reaction cavity 430. The removable lid 490 is then removed from the plate structure 410.

After forming the second product, the buffer solution in the tank 455 is pressurized to spill into the reaction cavity 430 via the conduit 456 for rinse. Then, the removable lid 490 is covered onto the supporting plate 410 to allow the adsorption pad 495 attached thereinside to adsorb the liquid in the reaction cavity 430. Lastly, the removable lid 490 is removed from the supporting plate 410.

Example 5

Figure 5A:
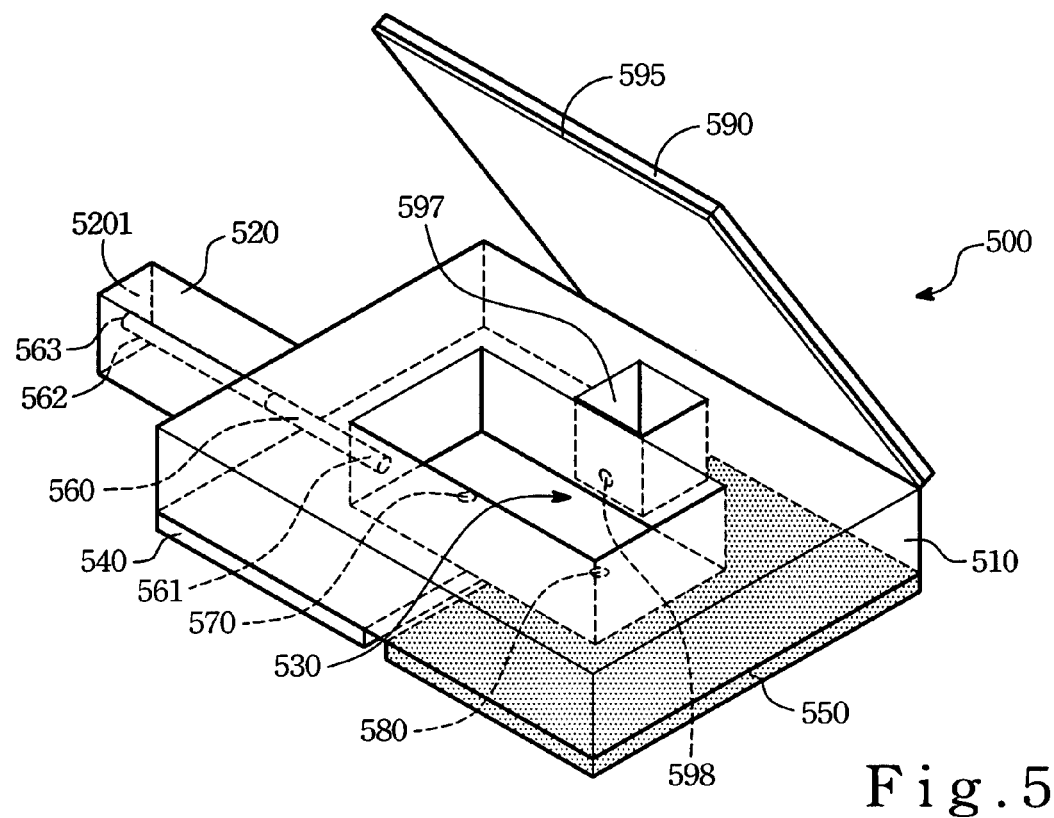
FIG. 5A shows a side view of an immunoassay cartridge according to the present invention.

Referring to FIG. 5A, a side view of an immunoassay cartridge 500 is shown herein. The immunoassay cartridge 500 includes a plate structure 510 and an extending portion 520 coupled thereto. In an embodiment of the present invention, the extending portion 520 and the plate structure 510 are made by a procedure of one-piece molding. In another embodiment, the extending portion 520 and the plate structure 510 are fabricated separately and then assembled together.

Within the plate structure 510 includes a reaction cavity 530, and at least one analyte-binding molecule is immobilized on the bottom surface of the reaction cavity 530. In one preferred embodiment of the present invention, the analyte-binding molecule(s) within the reaction cavity 530 is/are printed to form an array. In addition, the method of immobilizing the analyte-binding molecule in the reaction cavity 530 comprises physical adsorption, cross-linking, covalent binding, entrapment or any combination thereof.

One end 561 of a sample receiving end 560 is connected to the reaction cavity 530. The other end 562 of the sample receiving end 560 penetrates through the extending portion 520 and has an opening 563 on a sidewall 5201 of the extending portion 520. In this embodiment, the extending portion 520 is provided to protect the sample receiving end 560 from being broken.

A biological sample suspected of an analyte is received from the opening 563 and flows into the reaction cavity 530 via the sample receiving end 560. In another embodiment, the biological sample is loaded into the reaction cavity 530. That is, the sample receiving end 560 can be optionally omitted from the immunoassay cartridge 500 according to practical needs.

In a preferred embodiment of the present invention, the biological sample comprises a blood sample, a serum sample or a saliva sample. In addition, the sample receiving end 560 is a capillary.

In one preferred embodiment of the present invention, the analyte is an antigen and the analyte-binding molecule is a first antibody correspondingly. In another embodiment, the analyte-binding molecule is a ligand when the analyte is a protein.

The immunoassay cartridge 500 further comprises a first package 540 and a second package 550 filled with a recognizing molecule and a buffer solution, respectively. It is noted that the recognizing molecule is preferably a second antibody when the analyte is the antigen and the analyte-binding molecule is the first antibody. However, it is appreciated that these are not used to limit the score and the spirit of the present invention. One of differences between Example 5 and Example 3 is that the first package 540 in this example is located under the plate structure 510.

A first channel 570 within the plate structure 510 communicates the first package 540 and reaction cavity 530, whereas a second channel 580 connects the second package 550 and reaction cavity 530.

In one preferred embodiment of the present invention, the first channel 570 and the second channel 580 are both sealed by stoppers. When the first package 540 suffers the pressure, the recognizing molecule contained therein breaks through the stopper and spills into the reaction cavity 530. When the second package 550 suffers the pressure, the buffer solution contained therein breaks through the stopper and spills into the reaction cavity 530.

As described in Example 1, the immunoassay cartridge 500 further comprises a removable lid 590 capable of being covered onto the plate structure 510. On the inner surface of the removable lid 590 is lined with an adsorption pad 595. In one preferred embodiment of the present invention, the adsorption pad 595 is made of adsorbing materials like membranes, tissues, or polymers such as starch-acrylic acid graft copolymer, copoly (vinyl alchol-acrylic acid), cross-linking copolyacrylic acid or combinations thereof. It is appreciated that these are not used to limit the score and the spirit of the present invention.

When the immunoassay cartridge 500 is accommodated by an analyzer (not shown herein), the biological sample flowing into the reaction cavity 530 through the sample receiving end 560 reacts with the analyte-binding molecule immobilized in the reaction cavity 530, thus forming a complex of the analyte and the analyte-binding molecule.

Thereafter, the removable lid 590 is covered onto the plate structure 510 to allow the adsorption pad 595 attached thereinside to adsorb the liquid in the reaction cavity 530. Next, the removable lid 590 is removed from the plate structure 510.

After forming the complex of the analyte and the analyte-binding molecule, the buffer solution in the second package 550 is forced to break the stopper and spill into the reaction cavity 530 via the second channel 580 for wash.

Next, the used adsorption pad 595 should be replaced with a fresh one by the analyzer for avoiding contaminations. That is, the used adsorption pad 595 should be replaced with a fresh one every time when it is used to adsorb the liquid within the reaction cavity 530.

Thereafter, the removable lid 590 is covered to the plate structure 510 to allow the new adsorption pad 595 attached thereinside to adsorb the liquid in the reaction cavity 530.

In another embodiment, the adsorption pad 595 is directly installed in the analyzer instead of being attached on the removable lid 590. The purpose of the adsorption pad 595 is to adsorb the liquid within the reaction cavity 530 rapidly. Accordingly, various possible modifications and substitutions, without departing from the purpose, should be should be included in the present invention. After evacuating the liquid within the reaction cavity 530 using the adsorption pad 595, the removable lid 590 is removed from the plate structure 510.

Next, the first package 540 is automatically compressed to have the recognizing molecule, such as a gold-conjugated antibody, contained therein break the stopper and flow into the reaction cavity 530 via the first channel 570, thus forming a first product of the complex and the recognizing molecule. After that, the removable lid 590 is covered onto the plate structure 510 to allow the adsorption pad 595 attached thereinside to adsorb the liquid contained in the reaction cavity 530. The removable lid 590 is then removed from the plate structure 510.

Lastly, the second package 550 is automatically compressed again to force the buffer solution to spill into the reaction cavity 530 for rinse.

It is noted that, in another embodiment, a diameter of the first channel 570 is designed to allow the recognizing molecule to stay in the first package 540 and then spill into the reaction cavity 530 when the first package 540 is pressurized. A diameter of the second channel 580 is designed to allow the buffer solution to spill into the reaction cavity 530 when the second package 550 is pressurized. In other words, the stopper described above is absent in this embodiment.

Furthermore, the diameters of the first channel 570 and the second channel 580 are designed to avoid the liquid within the reaction cavity 530 leaking to the first package 540 or the second package 550.

In one preferred embodiment of the present invention, the third package 597 comprises a pit made within the plate structure 530 and a covering covered onto the pit. In another embodiment, the third package 597 comprises a container coupled to the plate structure 530 and a covering covered onto the container.

In the enzymatic immunoassay, the complex of the analyte and the analyte-binding molecule is bound with an enzyme. The enzyme-bound complex is then contacted with the signal molecule, e.g. a substrate, for the enzyme to produce a detectable substance.

As described above, a third channel 598 communicates the third package 597 and the reaction cavity 530. Accordingly, the third package 597 is adjacent to the reaction cavity 530.

In one preferred embodiment of the present invention, the third package 597 comprises a pit fabricated within the plate structure 510 and a covering covered onto the pit. Further, the third channel 598 is sealed by a stopper. When the covering of the third package 597 is pressurized, the signal molecule inside the third package 597 breaks through the stopper and flows into the reaction cavity 530. The covering is preferably made of polymer such as PDMS or PET (polyethylene terephthalate). The stopper is made of a wide variety of materials including silicon, polyvinyl alcohol (PVA), polystyrene (PS) or other polymers.

After forming the first product of the complex and the recognizing molecule, the signal molecule in the third package 597 is automatically pressed to break the stopper and flow into the reaction cavity 530 via the third channel 598, thus forming a second product of the first product and the signal molecule. Subsequently, the removable lid 590 is covered to the plate structure 510 to allow the adsorption pad 595 attached thereinside to adsorb the liquid in the reaction cavity 530. Then, the removable lid 590 is removed from the plate structure 510.

Lastly, the second package 550 is automatically pressed again to force the buffer solution to flow into the reaction cavity 530 for rinse. The second product is subjected to detect the concentration of the analyte in the biological sample.

It is noted that, in another embodiment, a diameter of the third channel 598 is designed to allow the signal molecule to stay in the third package 597 and then flow into the reaction cavity 530 when the third package 597 is pressed. In other words, the stopper described above is absent herein.

Figure 5B:
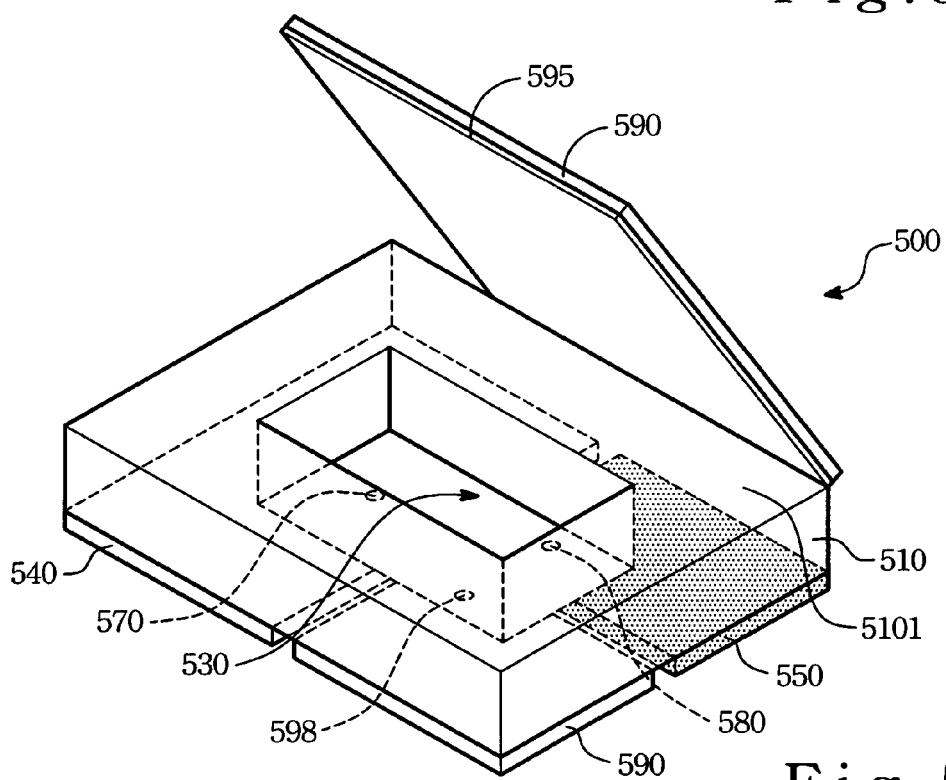
FIG. 5B shows a side view of an immunoassay cartridge according to the present invention.

Referring to FIG. 5B, the third package 597 is located under the plate structure 510. A third channel 598 communicating the third package 597 and reaction cavity 530 is sealed by a stopper. When the third package 597 is compressed, the signal molecule contained therein breaks through the stopper and spills into the reaction cavity 530, thus forming the second product of the first product and the signal molecule as described above.

In this case, a diameter of the third channel 598 is designed to avoid the liquid within the reaction cavity 530 leaking to the third package 597.

Example 6

Below, carcinoembryonic antigen (CEA) used in the immunoassay cartridge 400 of Example 4 is illustrated to elucidate how the immunoassay of the present invention works. It is appreciated that, however, the CEA system exemplified herein is not used to limit the score and the spirit of the present invention.

CEA, a 180 kD intercellular adhesion molecule expressed in high concentrations in the fetus but normally not found in adult serum because the synthesis of this protein ceases after birth. However reappear in a high concentration in the sera of patients with colorectal (57%), gastric (41%), hepatocellular (45%), pancreatic (59%) and biliary (59%) carcinoma. The serum concentration of CEA can also be elevated in benign diseases of the colorectum (inflammatory bowel disease 17%), stomach (chronic gastritis and peptic ulcer 14%), liver (cirrhosis and hepatitis 17%) and pancreas (21%). Elevated levels of CEA have also been observed in patients with inflammatory nonmalignant diseases like pulmonary emphysema, alcoholic cirrhosis, and pancreatitis and in heavy smokers. In contrast to cancer these elevations are transitory. The serum levels drop back into the normal range within a few weeks.

Before carrying out the immunoassay with the immunoassay cartridge, a biological sample suspected of the CEA is loaded into the reaction cavity 430.

When the immunoassay cartridge 400 is accommodated by the analyzer (not shown herein), the biological sample suspected of CEA flows into the reaction cavity 430 through the first channel 460 and reacts with a capture antibody, e.g. mouse anti-human CEA monoclonal antibody, immobilized in the reaction cavity 430. Hence, a complex of the CEA and the capture antibody is formed.

Thereafter, the removable lid 490 is automatically covered onto the supporting plate 410 to allow the adsorption pad 495 attached thereinside to adsorb the liquid in the reaction cavity 430. Next, the removable lid 490 is automatically removed from the supporting plate 410.

After forming the complex of the of the CEA and the capture antibody, the buffer solution, preferably 0.1 M phosphate buffer at pH 7.4, in the tank 455 is pumped to the reaction cavity 430 via the conduit 456 for rinse.

Thereafter, the removable lid 490 is automatically covered onto the supporting plate 410 to allow the adsorption pad 495 attached thereinside to adsorb the liquid in the reaction cavity 430. Then, the removable lid 490 is automatically removed from the supporting plate 410.

Next, the recognizing molecule, e.g. immunoglobulin (IgG) fraction of rabbit antiserum to human CEA, in the first package 440 is squeezed to break the stopper and flow into the reaction cavity 430 via the second channel 470, thus forming a first product of the complex and the recognizing molecule. After that, the removable lid 490 is automatically covered onto the supporting plate 410 to allow the adsorption pad 495 attached thereinside to adsorb the liquid contained in the reaction cavity 430. The removable lid 490 is then automatically removed from the plate structure 410.

After forming the first product of the complex and the recognizing molecule, the buffer solution in the tank 455 is pumped to the reaction cavity 430 via the conduit 456 for rinse. Then, the removable lid 490 is automatically covered onto the supporting plate 410 to allow the adsorption pad 495 attached thereinside to adsorb the liquid in the reaction cavity 430. Thereafter, the removable lid 490 is automatically removed from the supporting plate 410.

The detection process may be performed if the recognizing molecule has already conjugated with signal molecule(s) such as fluorophore(s), isotope(s), or gold particle(s).

Accordingly, the recognizing molecule, such as sheep anti-rabbit IgG antibody that conjugated with the signal molecule(s), is contained in the second package 450 and is squeezed to break the stopper and flow into the reaction cavity 430 via the third channel 480, thus forming a second product of the first product and the recognizing molecule (in other words, the first package 440 is absent in this embodiment). After that, the removable lid 490 is automatically covered onto the supporting plate 410 to allow the adsorption pad 495 attached thereinside to adsorb the liquid contained in the reaction cavity 430. The removable lid 490 is then automatically removed from the plate structure 410.

After forming the product, the buffer solution in the tank 455 is pumped to the reaction cavity 430 via the conduit 456 for rinse. Then, the removable lid 490 is automatically covered onto the supporting plate 410 to allow the adsorption pad 495 attached thereinside to adsorb the liquid in the reaction cavity 430. Lastly, the removable lid 490 is automatically removed from the supporting plate 410.

While the preferred embodiment of the invention has been illustrated and described, it is appreciated that various modifications, additions and substitutions can be made therein without departing from the spirit and scope of the invention.

What is claimed is:

1. A cartridge for sensing at least one analyte in a biological sample, comprising:
    a tank for containing a buffer solution;
    a supporting plate attached to the tank;
    a reaction cavity within the supporting plate and having at least one analyte-binding molecule immobilized therein, the biological sample is loaded into the reaction cavity and at least one complex of the analyte and the analyte-binding molecule is thus formed;
    a removable lid covering the reaction cavity, wherein the removable lid comprises an absorption pad adhered on an inside surface of the removable lid to adsorb the liquid in the reaction cavity;
    a conduit communicating the tank and the reaction cavity to allow the buffer solution to spill into the reaction cavity; a first package containing a recognizing molecule; and
    a first channel communicating the first package and the reaction cavity to allow the recognizing molecule to flow into the reaction cavity, thus forming a first product of the complex and the recognizing molecule.

2. The cartridge of claim 1, further comprising a sample loading chamber.

3. The cartridge of claim 2, wherein the sample loading chamber is made within the supporting plate.

4. The cartridge of claim 2, wherein the sample loading chamber is coupled to the supporting plate.

5. The cartridge of claim 2, further comprising a second channel communicating the sample loading chamber and the reaction cavity to allow the biological sample to flow into the reaction cavity.

6. The cartridge of claim 1, further comprising a second package containing a signal molecule.

7. The cartridge of claim 6, further comprising a third channel communicating the second package and the reaction cavity to allow the signal molecule to flow into the reaction cavity, thus forming a second product of the first product and the signal molecule.

* * * * *